(12) United States Patent
Balian et al.

(10) Patent No.: US 8,357,079 B2
(45) Date of Patent: Jan. 22, 2013

(54) DEVICES FOR INITIATING POSITIVE THINKING

(76) Inventors: Judith Balian, Encinitas, CA (US); Adrian Pelkus, Escondido, CA (US)

( * ) Notice: Subject to any disclaimer, the term of this patent is extended or adjusted under 35 U.S.C. 154(b) by 352 days.

(21) Appl. No.: 12/799,132

(22) Filed: Apr. 19, 2010

(65) Prior Publication Data
US 2010/0204541 A1    Aug. 12, 2010

Related U.S. Application Data

(63) Continuation-in-part of application No. 11/880,573, filed on Jul. 23, 2007, now abandoned.

(51) Int. Cl.
*A61M 21/00* (2006.01)
(52) U.S. Cl. .......................... 600/27; 600/26; 340/309.7
(58) Field of Classification Search .............. 600/26–28; 340/309.7; 128/897–898
See application file for complete search history.

(56) References Cited

U.S. PATENT DOCUMENTS

| 4,009,381 A | * | 2/1977 | Schreiber et al. | 362/571 |
| 5,306,228 A | * | 4/1994 | Rubins | 600/27 |
| 5,823,932 A | * | 10/1998 | Speigel | 600/26 |
| 6,326,881 B1 | * | 12/2001 | Dahl | 340/309.7 |
| 6,558,165 B1 | * | 5/2003 | Curry et al. | 434/236 |
| 2003/0149372 A1 | * | 8/2003 | Smith et al. | 600/532 |
| 2005/0215848 A1 | * | 9/2005 | Lorenzato | 600/27 |
| 2006/0047179 A1 | * | 3/2006 | Graves et al. | 600/27 |

* cited by examiner

*Primary Examiner* — Charles A Marmor, II
*Assistant Examiner* — Carrie R Dorna

(57) ABSTRACT

A device for initiating positive thoughts in an individual wherein the positive thought is not an implanted post-hypnotic suggestion. The device comprises housing for an energy source and an electronic circuit connected to an energy source affixed within the housing. The electronic circuit has an alerting means and a means for controlling the alerting means. The alerting means notifies the individual a determined number of times over a given period in an apparent random manner at a frequency of 10-12 Hz.

16 Claims, 3 Drawing Sheets

DEVICES FOR INITIATING POSITIVE THINKING

CROSS-REFERENCE TO RELATED APPLICATIONS

This application is a continuation in part of patent application Ser. No. 11/880,573 filed Jul. 23, 2007 now abandoned.

STATEMENT REGARDING FEDERALLY SPONSORED RESEARCH OR DEVELOPMENT

None

INCORPORATION-BY-REFERENCE OF MATERIAL SUBMITTED ON COMPACT DISC

None

BACKGROUND OF THE INVENTION (1) Field of the Invention

The present invention is a device that notifies the wearer to focus on positive thoughts or particular goals. More particularly, to devices that may be worn as jewelry or be placed on a desktop or a wall that alerts the wearer or user by, for example, producing a sound, a blinking light or by vibrating and thereby initiating conditioned thought responses previously formulated or established by the wearer which promote positive wellbeing.

(2) Description of Related Art

A variety of devices in the form of jewelry are available commercially that provide light and/or sound. For example, in U.S. Pat. No. 5,662,062 a ring is provided that comprises a circuit device comprising a light producing circuit, a sound producing circuit, a battery power supply and a switch that when activated causes the ring to produce light and sound for a predetermined amount of time. Correspondingly, U.S. Pat. No. 4,009,381 is a pin or broach comprising a plurality of individual filamentary light-conducting fibers whose ends converge at a light source which is connected to a power supply and controlled by a switch. When activated the filaments emit light from their ends, which are directed toward the observer. In addition there are a number of devices for the desktop or wall mounting that are ornamental and/or combine other functions such as a clock, calculator, thermometer, humidity meter, etc. However, none of these devices is an educational or learning tool and none alert the wearer of a particular thought or thought process.

Over the past century a significant amount of research has been conducted regarding the power of thought. A recent book regarding this process written by Rhonda Byrne called *The Secret* focuses on the law of attraction and the belief that one's positive thoughts are powerful magnets that attract wealth, health and happiness. The premise of the law of attraction is that one's thoughts eventually culminate in actual occurrences, which shape the events in the life of the person. Whether one's thoughts are negative or positive does not effect their culmination, merely the time spent thinking a particular thought increases its probability of occurring. Consequently, it is postulated that continued and consistent positive thinking would result in the proliferation of positive events for the person with such thoughts.

Unfortunately, people do not always focus on thinking a particular way and often times will concentrate on thoughts culminating from fear, worry or concern. Under the theory of the law of attraction, these consistent negative thoughts result in a greater chance of those negative events actually occurring.

Consequently there is a need for a method of reminding people to consider their thoughts at regular intervals as a way of training them to initiate consistent positive thinking or thought processes, thereby resulting in the increased probability of the occurrence of those positive events.

BRIEF SUMMARY OF THE INVENTION

A device for initiating positive thought in an individual wherein the positive thought is not an implanted post-hypnotic suggestion comprising a housing for an energy source and an electronic circuit connected to an energy source and affixed within the housing. The electronic circuit having an alerting means and a means for controlling the alerting means to notify the individual a determined number of times over a given period in an apparent random manner at a frequency of 10-12 Hz.

The device may be jewelry such as a bracelet, a ring, a watch, a fob, a lapel pin or a broach. It may be an item for a desktop or for mounting on a wall such as a decorative piece of art or a clock.

In one embodiment, the alerting means may be a light, a sound or a vibration. The means for controlling the alerting means may be a microchip that may be programmed to notify the user a determined number of times over a given period of time in an apparent random manner. Preferably that notification is not less than one alert per day and not more than ten alerts per hour. Most preferably the number of alerts over a given period of time is not less than one per hour and not more than three per hour.

In another embodiment, the alerting means is a light. The light may be produced from an incandescent bulb or an LED. It may be observed directly from the source, or it may be transmitted through fiber optical cable.

In other embodiments, the device may further comprise a light cover and/or a switch between the energy source and the electronic circuit so that the device may be activated or deactivated to conserve energy.

In another aspect of the present invention, a method of alerting an individual to initiate positive thought is provided comprising the steps of affixing the jewelry to the individual or placing the device on a desktop or mounting the device on a wall, setting the alert notification frequency and activating the device in any order.

In yet another aspect of the present invention, a system for initiating positive thought is provided comprising the device, an instruction booklet on the operation of the device, and a compact disc demonstrating the use of the device.

DETAILED DESCRIPTION OF THE INVENTION

Figure 1:
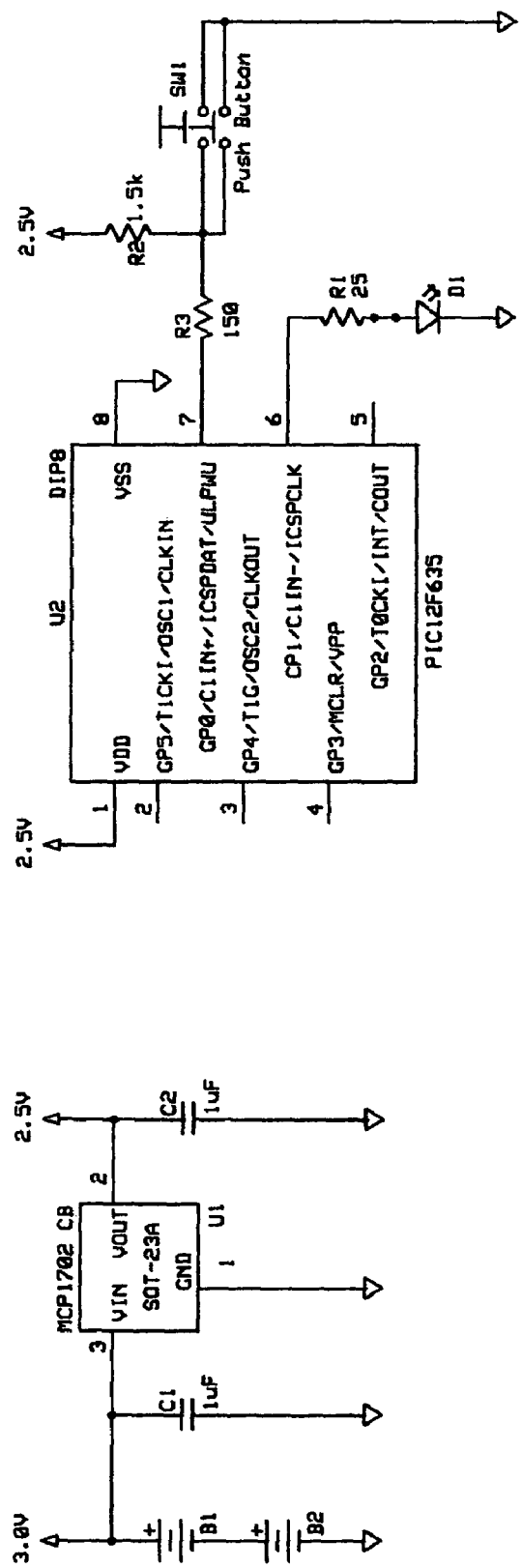
FIG. 1 is an electronic diagram of the circuitry of one preferred embodiment of the present invention as a piece of jewelry particularly a bracelet.
Figure 2:
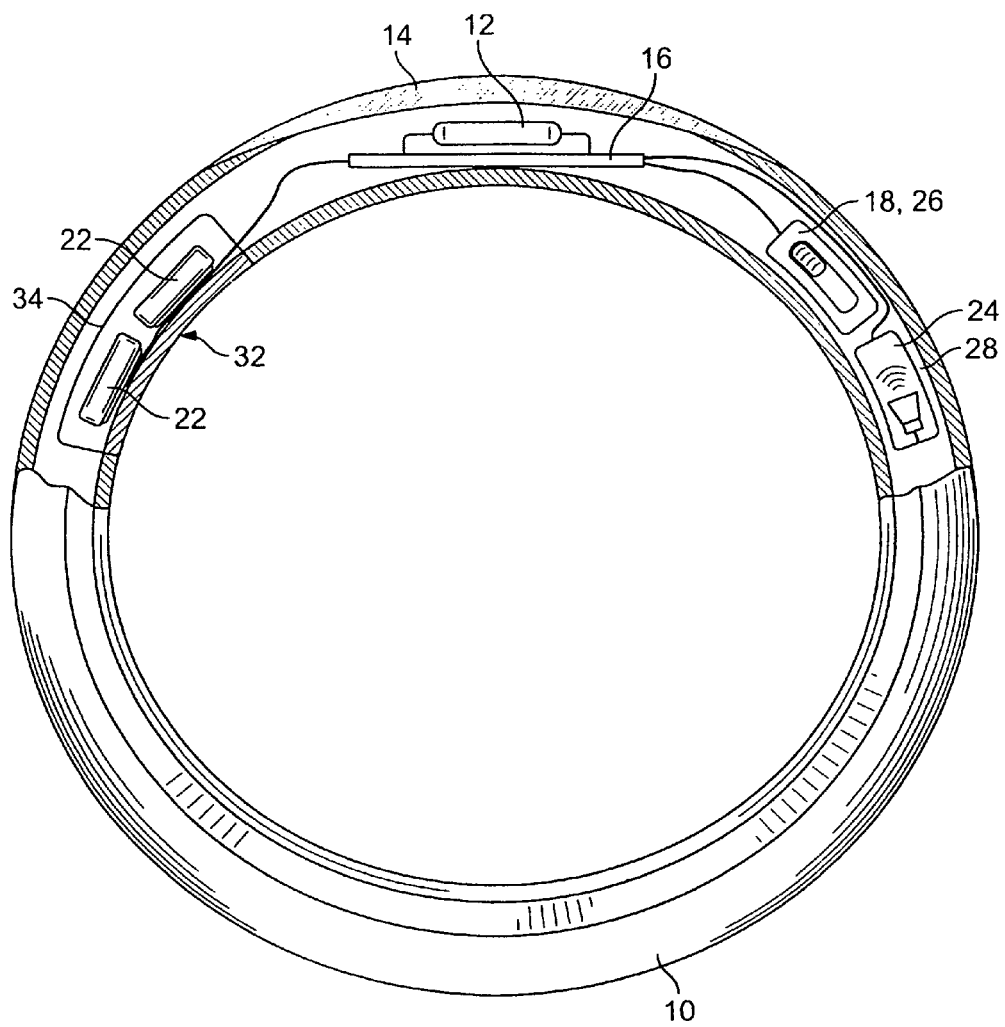
FIG. 2 is a cross sectional view of one embodiment of the present invention.
Figure 3:
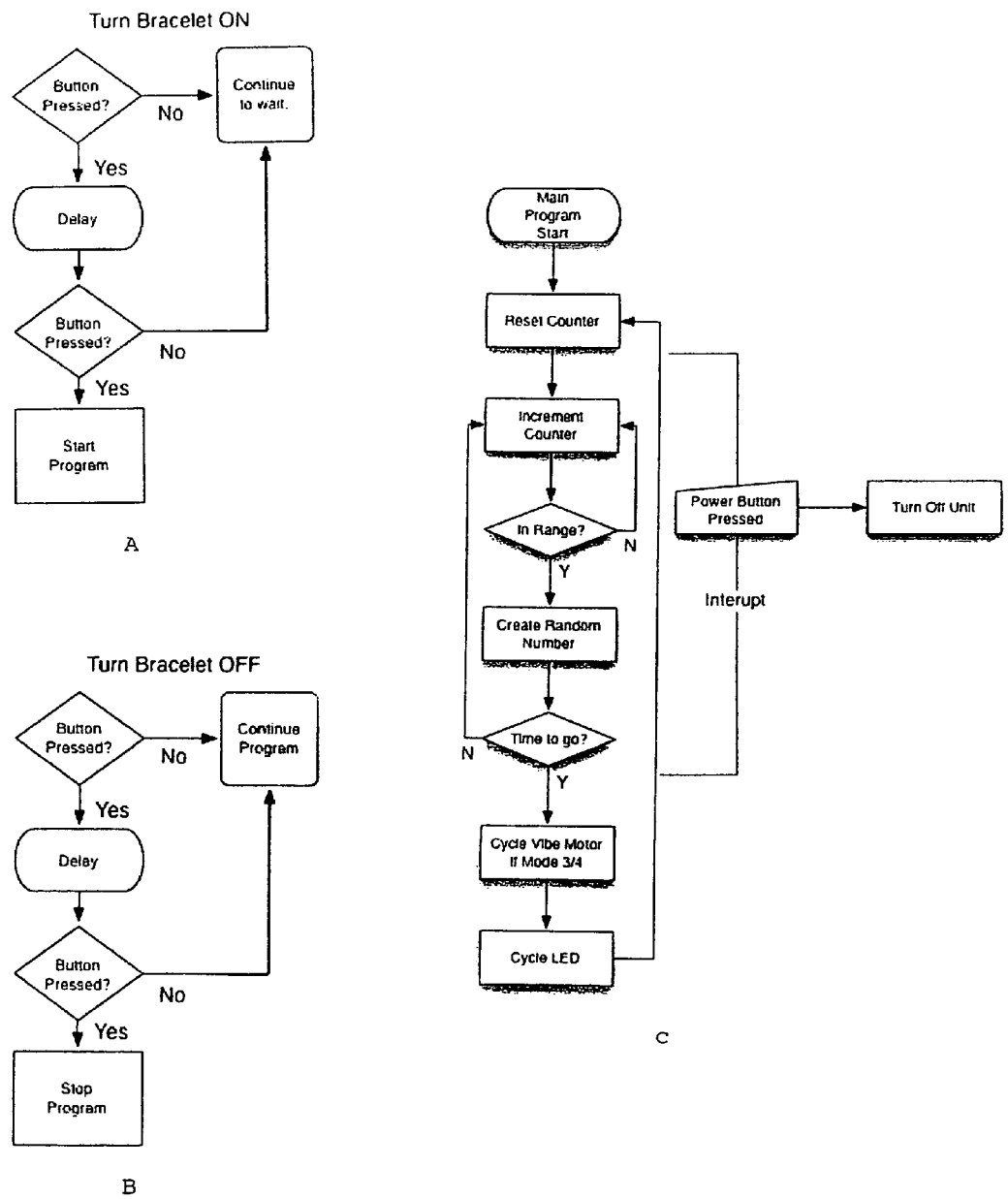
FIG. 3 (A) is a schematic diagram of turning on the devices; (B) is a schematic diagram of turning off the device; and (C) is a schematic diagram of the operation of the device.

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "alerting means" as used herein refers to any means by which the user of the present invention may be alerted or notified. Such a stimulus can be visual, auditory or by tactile sensation. For example the alerting means may be a light emitting diode, an acoustic emitter or an electromagnetic vibrator.

The term "means for controlling" as used herein refers to a microchip that provides one or more programs that may be selected for activating the alerting means in a seemingly or apparent random manner. The program selection may be instituted prior to sale or a selection capability may be provided on the device for the user. In a preferred embodiment when the alerting means is a light, the means for controlling may not only activate the light to alert the wearer but may also emit the light at a frequency that appeals to the alpha brain waves of the wearer. Where such a frequency of an acoustical or tactile nature are known, the means for controlling may provide sound or vibration that initiates or appeals to the alpha brain wave state of the wearer.

The present invention may be utilized as an educational and/or training tool. The concept of alerting an individual in a random, or seemingly random manner to initiate a particular thought or thought pattern is based on theories of classical conditioning from the behavioral psychology, which explains that a given stimulus can elicit a particular response, the learning theory of contiguity, which explains the tendency of association of a stimulus and response that are connected in time and/or space and operant conditioning which is the use of consequences to modify the occurrence and form of behavior. Operant conditioning may be distinguished from Pavlovian conditioning because it deals with the modification of voluntary behavior through the use of consequences, while Pavlovian conditioning deals with the conditioning of behavior so that it occurs under new antecedent conditions. These theories have been applied to human learning and are well known in the fields of psychology and education. Recent trends in behaviorism have tended to focus on cognition and motivation, which were avoided in early studies. Both these are key factors in maintaining and reinforcing a particular desire thought or thought pattern.

Classical conditioning, which has been used extensively in advertising, uses a stimulus-response approach to change behavior. The stimulus is the environmental event such as for example, the flashing of a light, the initiation of a recognized sound or a tactile stimulation, and the response is the corresponding action or specific behavior by the user such as for example, the mental, physical or verbal act that promotes a particular thought or thought pattern. Verbal or mental acts may be the recitation of a mantra or affirmation.

The major theorists for the development of operant conditioning are Edward Thorndike, John Watson, and B. F. Skinner. They proposed that learning is the result of the application of consequences. More specifically, learners begin to connect certain responses with certain stimuli. This connection causes the probability of the response to change resulting in learning. Where classical conditioning illustrates stimulus to response or S-->R learning, operant conditioning is often viewed as response to stimulus or R-->S learning since it is the consequence that follows the response that influences whether the response is likely or unlikely to occur again.

Behaviorist theories state that virtually any behavior: academic, social, or psychomotor can be learned or modified through operant conditioning. According B. F. Skinner (Skinner, B. F. (1953). Science and Human Behavior. New York: The Free Press), a response followed by a reinforcer, such as a reward, is strengthened and more likely to occur again. Because the user of this device is self-motivated, the "reward" in this case is intrinsic rather than external, the intrinsic reward being the thoughts or thought patterns for example, positive feelings generated by the user as a result of his actions. Further, according to the classic theories of Edward Thorndike, (Thorndike, E. L. (1935). The Psychology of Wants, Interests and Attitudes. New York: Appleton-Century Crofts), responses to a situation that are satisfying are strengthened while responses that are uncomfortable are weakened. The desired thoughts or thought patterns that are initiated by the user at the activation of the stimulus create the former situation.

Extinction of a learned response occurs in classical conditioning when a conditioned stimulus repeatedly occurs without the presence of the unconditioned stimulus it had been paired with. In operant conditioning, extinction is the decline of an operant response when it is no longer reinforced in the presence of its discriminative stimulus. However, it is possible after extinction of a behavior has occurred to reestablish the response if the conditioned stimulus is presented again. Therefore, the user who has developed the desired thought or thought patterns and discontinues the use of the device may recover the conditioned response by reinstituting its use.

B. F. Skinner found that reinforcement of conditioned responses obtained better results when the stimulus was provided in a random or variable schedule than a fixed interval schedule. True mathematical randomization is not necessary only that the user not be able to anticipate the initiation of the preceding stimulus. It was also found that a device using randomization of the intervals of flashing of approximately every 20 minutes or every 60 minutes was sufficient to avoid predictability on the part of the user.

Hans Berger first recorded alpha brain waves, which range in frequency from 8 to 12 Hz, in electroencephalograms of human subjects in the 1920's. Subsequent researchers have shown that people with high levels of Alpha brain waves are less anxious, more motivated and more clear thinking than those with lower incidence of Alpha waves. These waves are now associated with greater intelligence, enhanced creativity, improved mind/body coordination and agility, and less stress. Alpha is considered to be an optimal brain wave state for many activities.

In a recent light therapy study for attention deficit, hyperactivity disorder or "ADHD", dyslexia and autism it was found that spending twenty minutes sitting in front of a flashing light help children learn to read or control themselves. By exposing participants to a flashing light for one second, researchers in Oxford found that participants were better able to recall a list of trigrams (semi-random groups of three letters). Most importantly the improvements only happened when the lights were flashed at frequencies on or around 10.2 Hz, a frequency related to the brain's alpha waves and believed to be relevant to memory functions.

Two U.S. patents describe devices utilizing some of these principles. U.S. Pat. No. 5,823,932 provides a device that produces a visual, audio or tactile signal that when received by the subject triggers the implanted positive or aversive suggestion. The apparatus and method are intended for use with subjects who have undergone hypnotherapy sessions to implant positive or aversive post-hypnotic suggestions, such as the hypnotherapy treatment method disclosed in U.S. Pat. No. 5,425,699. This method entails providing hypnotherapy treatment to the patient, by an in-person therapy session or by pre-recorded audiotapes or compact disks. These post-hypnotic suggestions are linked to a signal or trigger that is later utilized to activate the implanted suggestion.

U.S. Pat. No. 5,306,228 provides a device for inducing brain waves with a predetermined synchronization frequency using both flashing lights and pulsating tones utilizing differential frequencies in the alpha wave range (10 Hz). For example, if the base frequency of the audio tone in the ear phones is chosen to be 440 Hz and the desired brain wave frequency is 10 Hz, the second frequency would be chosen to be 440 Hz plus or minus 10 Hz. Alternatively, the user will see lights that flash alternately left-right at a frequency of 10 Hz, and will hear a tone that switches back and forth between the left and right ears at a frequency of 10 Hz. Additionally, the tone heard in the one ear will be 10 Hz higher than the tone heard in the other ear. This patent suggests that once the subject's brain waves are synchronized, they are better able to receive subliminal or audible audio messages.

However, unlike U.S. Pat. No. 5,823,932, the present invention does not require an implanted post-hypnotic suggestion, nor does it act as a trigger that initiates the implanted positive or aversive suggestion in the subject. In addition, unlike U.S. Pat. No. 5,306,228, the present invention does not use both visual and audio stimuli at differential frequencies to initiate synchronization of the subject's brain waves.

Specifically, the present invention uses a visual, audio or tactile signal at an alpha brain wave frequency of 8-12 Hz to initiate positive thought in an individual whose positive thought is not an implanted post-hypnotic suggestion.

In one embodiment, the device is prepared in the form of jewelry that may be worn by the user or as a desktop ornament or item that may be mounted on a wall. The device comprises a housing for an energy source and an electronic circuit connected to an energy source and affixed within the housing. The electronic circuit has an alerting means and a means for controlling the alerting means to notify the user a determined number of times over a given period in an apparent random manner.

The device of the present invention may be provided in a variety of configurations such as jewelry or a desktop or wall mounted ornament. For example, the device may take the form of a ring, a bracelet, a watch, a broach, a necklace, a fob, or a lapel pin. Alternatively, it may appear as a desk clock or other desktop device or ornament. In addition it may be provided in a wall-mounted configuration such as a clock or other ornamental design. Correspondingly, the selection of the configuration of the device will be determined based on the type of alerting means utilized in the housing. For example, if the alerting means were a light, it would be preferred that the device be in a location at which the wearer would be able to see the alert when activated. More specifically, if the device were jewelry, it would be preferable that the device be configured as a bracelet, ring or watch rather than a necklace or broach so that it may be more easily seen or observed by the wearer. Correspondingly, if the alerting means was a vibrator it would be preferable that the device be in touch or in close contact to the skin so that the vibration could be easily felt such as a necklace or bracelet. Alternatively, if the alerting device were to produce an auditory sound it would be preferable that the device be in a location that would increase the wearer's ability to hear the emitted sound such as a broach or necklace.

The actual ornamentation aspect of the device's configuration, such as for example, its design or the incorporation of gemstones, its structural elements based on the configuration selected such as for example a circular band for a ring, a chain loop for a necklace, or band for a watch, or the composition of the structural elements and/or ornamental aspects such as gold, silver or platinum, may vary substantially based on the desires and preferences of the wearer. In any and all configurations selected, the device 10 of the present invention will comprise housing 34 for an energy source 22 and an electronic circuit 16.

The housing 34 will provide a cavity for placement of the energy source 22 and a cover 32 for securely retaining the energy source 22 in the cavity. The cavity may be provided in a variety of sizes/shapes and will depend on the configuration of the device 10 and the size/shape of the energy source 22 utilized. Preferably small energy sources 22 will be used such as hearing aid or watch batteries when the configuration does not provide sufficient space for a larger battery. Such batteries may be obtained from a number of suppliers such as Beltone Electronics Corp. (Glenview, Ill.), Starkey (Eden Prairie, Minn.) and Siemens (New York, N.Y.). Correspondingly, larger batteries such as those used in cameras may be used in configurations capable of providing adequate housing. Such batteries may be obtained from a number of suppliers such as Energizer (Madison, Wis.) and Powermax (Rancho Cucamonga, Calif.). The battery will be connected to the electronic circuit to provide energy to the alerting means via the control means. Depending on energy usage, the device 10 of the present invention may further comprise a switch between the energy source 22 and the electronic circuit 16 so that the alerting means can be rendered inactive thereby conserving energy. The battery cover 32 may be provided in a variety of configurations, but is preferably a twist lock or press cover with a rubber seal similar to that used for watches to prevent moisture from entering the housing.

A variety of batteries, available commercially, may be utilized with the present invention. They may be selected based on the energy required to activate the electronic circuit 16, the size and shape of the housing that can be provided by the configuration selected and to achieve the longest operation time between battery replacements.

The electronic circuit 16 will comprise the alerting means connected to a programmable microchip 26 having one or more programs that may be selected for desired alerting frequencies and may further comprise a selection means for initiating the desired alerting program. One example of an electronic circuit 16 that may be utilized with the present invention is shown in FIG. 1.

The alerting means may be any method of notifying the wearer to initiate a desired thought or thought process. For example, such alerting means may be visual 12, acoustic 24 or tactile 28. Visual alerts may be provided by a light source such as an incandescent light or a light emitting diode (LED). A variety of LED's that emit a light visible to the wearer may be utilized with the present invention. In FIG. 1, an amber 20a AP2012SYCK 2.0×25 mm Smd Chip LED (Kingbright City of Industry, CA) is provided as an example of a light that may be utilized with the present invention. A variety of light emitting diodes may be utilized with the present invention including those sold by Panasonic, Matsushita Electric Industrial Company, Ltd., Kyoto, Japan part no.: LN01401C) or OPTEK (Carrolton, Tex. part no.: OVFSAAC8). Sound alerts may be provided by an acoustic emitter 24 such as those presently used in microelectronic devices such as greeting cards and beepers. A variety of acoustic emitters 24 may be utilized with the present invention and may be obtained from Dongson Technology Company, Ltd. (Cheung Sha Wan Kowloon, Hong Kong, Series Small Type SMD buzzer part no.: DSTB-404018S), Projects Unlimited (Dayton, Ohio, 7 khz 10 mm round buzzer part no.: AB1070B) or SPK Electronics Company, Ltd. (Taipei, China, buzzer part no.:

HC12). An electromagnetic vibrator 28 such as those used in cell phones and pagers may provide tactile alerts. A variety of acoustic emitters 24 may be utilized with the present invention and may be obtained from Suntech Development Company, Ltd. (Tsuen Wan, Hong Kong vibrator part no.: S6D1), AL Goodwell Industries Ltd. (Quarry Bay, Hong Kong buzzer as vibrator, part no.: AL14075MT-P) and SPK Electronics Company, Ltd. (Taipei, China, buzzer as vibrator part no.: HCM12-X). If the alerting means desired is a light 12, the device 10 of the present invention may further comprise a light cover 14 to protect the light from damage while worn. The cover may also function as a lens either focusing or dissipating the light emitted so that the alert may be more clearly visible to the wearer. Alternatively the cover may be provided in a variety of colors and/or in a press or snap fit configuration so that the wearer may replace or select a desired color for the alert. Alternatively, if the alerting means is an acoustic emitter, the device 10 may further comprise a means for selecting a desired alert sound. For example, the programmable microchip may further have a selection of sounds that the wearer may select when programming the device 10.

The programmable microchip or microcontroller may have one or more programs that may be selected for desired alerting frequencies and may further comprise a selection means for initiating the desired alerting program. A variety of microchips that perform this function may be utilized provided they have sufficient memory to maintain a desired number of programs for the alerting frequency selections and capable of activating the alerting means based on the program selected. FIG. 1 shows a schematic diagram of one proposed electronic circuit 16 that may utilized in the present invention. In the diagram the programmable microchip such as the IC MCU FLASH 1KX14 8SOIC PIC12F635-E/SN microcontroller (Microchip Technology, Inc. Chandler, Ariz.) U2 may be used to control the alerting means directly based on the program selected. A variety of microchip controller may be utilized such as that sold by Cypress (San Jose, Calif., part no.: CY8C21123-24SXI), Atmel (San Jose, Calif., part no.: ATTINY85-20SI) or Freescale Semiconductor, Inc. (Austin, Tex. part no.: MC68HC908QT4CDW). In addition a voltage regulator may be utilized to control the power provided to the programmable microchip. A variety of voltage regulators may be utilized to perform this function. In the diagram an IC LDO REG 250MA 2.5V SOT-23A (Microchip Technology, Inc. Chandler, Ariz.) U1 regulator has been selected as an example of one type of voltage regulator that may be utilized in the present invention.

The programs provided on the programmable microchip will be limited by the microchip's capabilities and the complexity of the selection processes provided to the wearer. The system may be simple, comprising a single program of randomly (seemingly randomly) alerting the wearer a set number of times within an hour, such as for example 3 times. A more complex system may provide a number of programs from which the wearer may select that vary the alerting frequency from as little as once per day to as much as four times per hour. Such a system may be provided in a similar manner as the programming of a car radio or other small electronic devices such as alarm clocks. Systems of this sort often provide a single push button. To activate the device 10 the button is pushed and the device becomes operational. Pressing the button again and holding the button until a visual element begins to flash such as the image on a viewing screen or a light activates the devices 10 program mode. Once flashing, a program can be selected by pressing the button the number of times until the program desired is displayed on the view screen or for a set number of times indicated in the instruction manual for the desired program. Finally the button is pressed a final time and held until the blinking screen or light ceases to blink or extinguishes. Complicated systems that allow the wearer to select the program for frequency of alerting, to program the activation and deactivation of the device 10, and/or to control the frequency of the alerting means are also contemplated.

Certain frequencies whether of light, vibration or sound can have certain measurable effects on humans and animals alike. The present invention utilizes these particular frequencies to re-institute or remind the wearer of pre-established positive thoughts and thought processes. It is currently believed that the maintaining of positive thoughts is what creates a positive environment for the thinker. With light, it was found that the ability to memorize groups of three letters was significantly enhanced by the flashing of a light at or around 10.2 Hz. This correlated with the frequencies recorded for alpha brain waves of from 8 to 12 Hz which had previously been associated with increased intelligence, enhanced creativity and improved mind/body coordination and agility. When the alerting means is a light, it is preferable that the light flash at or about this frequency to activate the alpha brain wave state of the wearer. Specifically, these frequencies include 8 Hz, 9 Hz, 10 Hz, 11 Hz, 12 Hz, 8-9 Hz, 9-10 Hz, 10-11 Hz 11-12 Hz, 8-10 Hz, 9-11 Hz, 10-12 Hz, 8-11 Hz and 9-12 Hz. Correspondingly, vibrations or sounds that activate or appeal to alpha brain wave functions, or other brain wave states that might be beneficial to the wearer, may be utilized, and are contemplated, by the present invention.

The number of times that a user is alerted will depend on the notifications required to maintain a desired state of positive thought. Correspondingly, the effectiveness of training should reduce the number of required alerts. For example, an individual who has not practiced positive thinking before obtaining the device 10 may desire a higher frequency of notifications or alerts, such as 3 to 4 times hourly. However, those who have practiced positive thinking may require a lower frequency of notifications such as once every couple of hours. A frequency select mode or dial adjust may be provided to allow the user to vary the number of alerts per given time period. This will increase the effectiveness of the devise by allowing the user to increase or decrease the number of alerts necessary to maintain his or her positive state of mind during a given time period.

To begin using the device, the user turns on the jewelry or desktop or wall mounted device by activating the on/off switch. The type of on/off switch may vary and could be, for example, a push button or dial. Once the device is activated, the desired frequency of alerting may be selected or the device will revert to a default frequency which may be set within the device or may be the last program selected. This may be done by for example, pressing the on/off button and holding the button down until the alerting means blinks, beeps or vibrates intermittently. This will activate the program selection mode. The on/off button is then pressed the desired number of times based on the instruction manual to select the specified number of alerts per time period. For example, the manual may provide a three program option wherein pressing the button once provides four alerts per hour or pushing the button twice which provides 2 alert per hour and pushing the button three times initiate the program to alert the wearer once per hour. Once the alerting frequency has been selected the program is set by pressing and holding the button once again until the light stops flashing the beeping stops or the vibration ceases.

Once a program has been set it re-establishes the selection button as an on/off switch and pressing it again will deactivate the device.

The invention claimed is:

1. A device for initiating positive thought in an individual wherein the positive thought is not an implanted post-hypnotic suggestion comprising:
   a) a housing for an energy source; and
   b) an electronic circuit connected to an energy source and affixed within said housing, said electronic circuit having an alerting means and a means for controlling said alerting means to notify the individual a determined number of times over a given period of time in an apparent random manner at a frequency of 10-12 Hz wherein said alerting means is a light and wherein said alerting means does not trigger and is not associated with an implanted post-hypnotic suggestion.

2. A device according to claim 1 wherein said device is jewelry selected from the group consisting of a bracelet, a ring, a watch, a fob, a lapel pin and a broach.

3. A device according to claim 2 wherein said alerting means is a light that flashes at a frequency of 10 Hz for a desired period of time.

4. A device according to claim 3 wherein said light is an LED light.

5. A device according to claim 3 wherein said jewelry further comprises a light cover.

6. A device according to claim 3 wherein said light is transmitted by optical fibers.

7. A device according to claim 1 wherein said device is for a desktop or for wall mounting.

8. A device according to claim 1 wherein said alerting means is a light and further emits a sound or a vibration.

9. A device according to claim 1 wherein said means for controlling said alerting means is a microchip that may be programmed to notify the user a determined number of times over a given period of time in an apparent random manner.

10. A device according to claim 9 wherein said determined number of times over a given period of time is not less than about one alert per day.

11. A device according to claim 9 wherein said determined number of times over a given period of time is not more than about ten alerts per hour.

12. A device according to claim 9 wherein said determined number of times over a given period of time is not less than about one alert per hour.

13. A device according to claim 9 wherein said determined number of times over a given period of time is not more than about three alerts per hour.

14. A device according to claim 1 further comprising a switch between said energy source and said electronic circuit.

15. A method of alerting an individual to initiate positive thought wherein the positive thought is not an implanted post-hypnotic suggestion utilizing a device comprising a housing for an energy source, and an electronic circuit connected to an energy source and affixed within said housing, said electronic circuit having an alerting means and a means for controlling said alerting means to notify the individual a determined number of times over a given period of time in an apparent random manner at a frequency of 10-12 Hz wherein said alerting means is a light and wherein said alerting means does not trigger and is not associated with an implanted post-hypnotic suggestion said method comprising the steps of:
   a) locating said device in proximity to said individual; and
   b) activating the device.

16. A system for alerting an individual to initiate positive thought wherein the positive thought is not an implanted post-hypnotic suggestion comprising the device according to claim 1, an instruction booklet on the operation of said device, and a compact disc demonstrating the use of said device.

* * * * *